United States Patent
Hilborne et al.

[11] Patent Number: 5,964,738
[45] Date of Patent: Oct. 12, 1999

[54] INFUSION SET INCLUDING A CLOSURE MEANS

[75] Inventors: David G. Hilborne, Dunstable; Roger O'Brien, Watford, both of United Kingdom

[73] Assignee: Sims Graseby Limited, Hertfordshire, United Kingdom

[21] Appl. No.: 08/765,515
[22] PCT Filed: Jun. 29, 1995
[86] PCT No.: PCT/GB95/01545
§ 371 Date: Apr. 21, 1997
§ 102(e) Date: Apr. 21, 1997
[87] PCT Pub. No.: WO96/00598
PCT Pub. Date: Jan. 11, 1996

[30] Foreign Application Priority Data
Jun. 30, 1994 [GB] United Kingdom ............. 9413193

[51] Int. Cl.⁶ .................. A61M 5/00; F16K 7/04
[52] U.S. Cl. ................. 604/249; 604/250; 251/7
[58] Field of Search ........................ 604/246, 249, 604/250, 256, 33, 34; 251/4, 7

[56] References Cited

U.S. PATENT DOCUMENTS

| | | |
|---|---|---|
| 2,889,848 | 6/1959 | Redmer ........................... 251/7 |
| 4,586,691 | 5/1986 | Kozlow .......................... 251/7 |
| 4,689,043 | 8/1987 | Bisha ........................... 604/250 |
| 4,932,629 | 6/1990 | Rodomista et al. ................ 251/4 |
| 5,017,192 | 5/1991 | Dodge et al. ................... 604/250 |
| 5,401,256 | 3/1995 | Stone et al. ................... 604/250 |
| 5,453,098 | 9/1995 | Botts et al. .................... 251/7 |

FOREIGN PATENT DOCUMENTS

| | | |
|---|---|---|
| A-319279 | 7/1989 | European Pat. Off. . |
| A-510881 | 10/1992 | European Pat. Off. . |
| A-569030 | 10/1993 | European Pat. Off. . |

*Primary Examiner*—Wynn Wood Coggins
*Assistant Examiner*—Sharon Finkel
*Attorney, Agent, or Firm*—Price, Heneveld, Coopler, DeWitt and Litton

[57] ABSTRACT

An infusion set (10,12) comprises a first part (10) housing a pump and control means and a second part (12) housing a replaceable infusate reservoir (14) with an integral infusion line (16). An anti-freeflow sliding member (26) has an opening (28) through which the infusion line (16) passes, and is slidable between a first open position and a second closed position by detaching the parts.

21 Claims, 2 Drawing Sheets

INFUSION SET INCLUDING A CLOSURE MEANS

TECHNICAL FIELD

The present invention relates to an infusion set including a closure means for closing an infusion line, for example in a medical apparatus.

SUMMARY OF THE INVENTION

Such closure means are often provided with or incorporated in medical infusion sets and similar equipment, to prevent the free flow of infusate which may otherwise occur, for example, when an empty infusate reservoir or cassette is replaced with a full one, or when, in a pumped system, an infusion line is removed from engagement with the pump.

According to the present invention there is provided an infusion set comprising a first part, a second part for containing an infusate reservoir and infusion line, the parts been releasably attachable together, and means for closing the infusion line, the closure means being operable, by detachment of the parts, to close the infusion line. The invention therefore provides a simple and reliable anti-freeflow mechanism.

The closure means may be slidably mounted on the second part between a first, open infusion line position and a second, closed infusion line position. The infusion line may pass through an opening in the closure means and the closure means may be mounted such that in the first position the infusion line passes through a portion of the opening of dimension great enough to allow flow of infusate through the infusion line and in the second position the infusion line passes through a portion of the opening having a dimension sufficiently less than the diameter of the infusion line to occlude the infusion line. In the first position, therefore, infusate can flow freely, whereas in the second position, the infusion line-is constricted at the point at which it passes through the opening, preventing the flow of infusate. The opening may be bounded by the closure member or may be unbounded at at least one end.

The closure means may have a tongue with a detent arranged to engage a projection on the first part to slide the closure means from the first to the second position as the parts are pulled apart and further arranged to release the closure means when the parts are fully detached. The tongue and detent may be arranged to engage the projection on the first part to slide the closure means from the second position to the first position when the parts are re-attached.

The infusion set may further include a tool adapted for manual operation of the closure means.

The first part may house a pump for pumping infusate from the infusate reservoir.

Accordingly, a two-part infusion set consists, for example, of a pump unit comprised within one part, and an infusate reservoir and flexible infusion line comprised within the other part, the two parts being adapted to fit together in use. In operation, the flexible infusion line in the second part is engaged by the pump in the first part to permit the infusate to be pumped from the infusate reservoir out through the infusion line to a patient. To prevent free flow of infusate to the patient, as might otherwise occur when the first, pump, part is detached from the second, reservoir, part, means are provided operative upon detachment of the two parts, to close the infusion line and to retain it in a closed condition. In addition to preventing unwanted infusion, the infusion line can then be detached from the patient without the need to manually close off the line to prevent infusate spillage.

BRIEF DESCRIPTION OF THE DRAWINGS

The invention will be described by way of example with reference to the embodiment illustrated in the accompanying drawings of which.

DETAILED DESCRIPTION OF THE INVENTION

Figure 1:
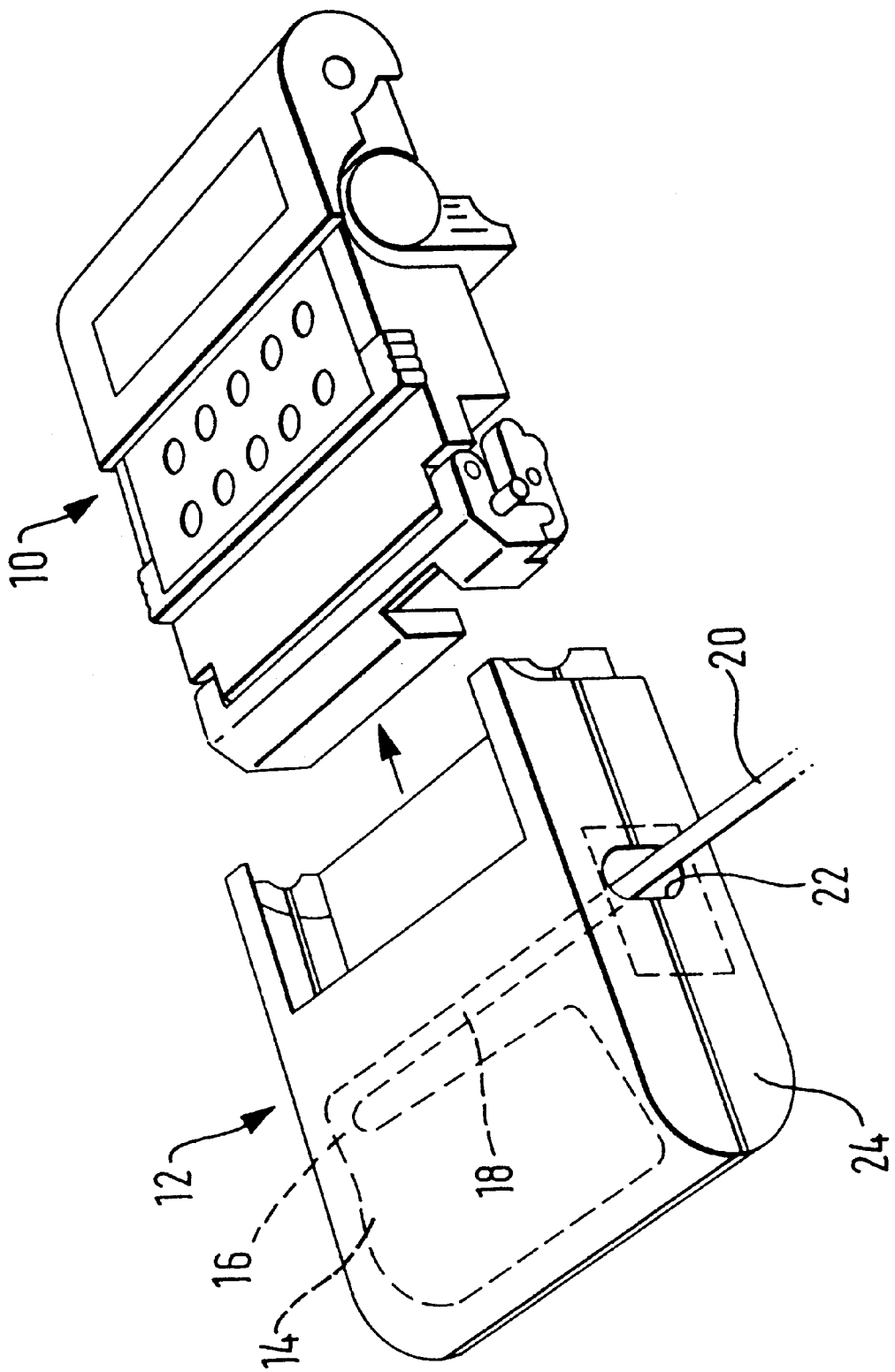
FIG. 1 is a perspective view of a two-part portable infusion pump.

Referring to the drawings, the two-part infusion pump comprises a first part 10, housing a pump and control means, together with an associated battery for powering both; and a second part 12, consisting of an upper and a lower half assembled together, attachable to and detachable from the first part 10, the second part 12 housing a replaceable infusate reservoir 14, with an integral infusion line 16.

The infusion line 16 has an aligned portion 18 which is engaged by the pump mechanism of the pump of part 10, and a portion 20 leading through exit port 22 in wall 24 of part 12. Portion 20 of infusion line 16 may be terminated by means of a luer coupling (not shown) or other attachment to permit ready access to an infusion site.

In operation, the two parts 10 and 12 are attached together, in which position the aligned portion 18 of the infusion line 16 is engaged from one side by a platen carried by the first part 10, and from the other by the pump fingers of the pump carried within part 10, such that progressive operation of the pump fingers upon portion 18 produces a peristaltic pumping action, pumping infusate from the reservoir 14 through portion 20 of infusion line 16 to the patient.

Figure 2:
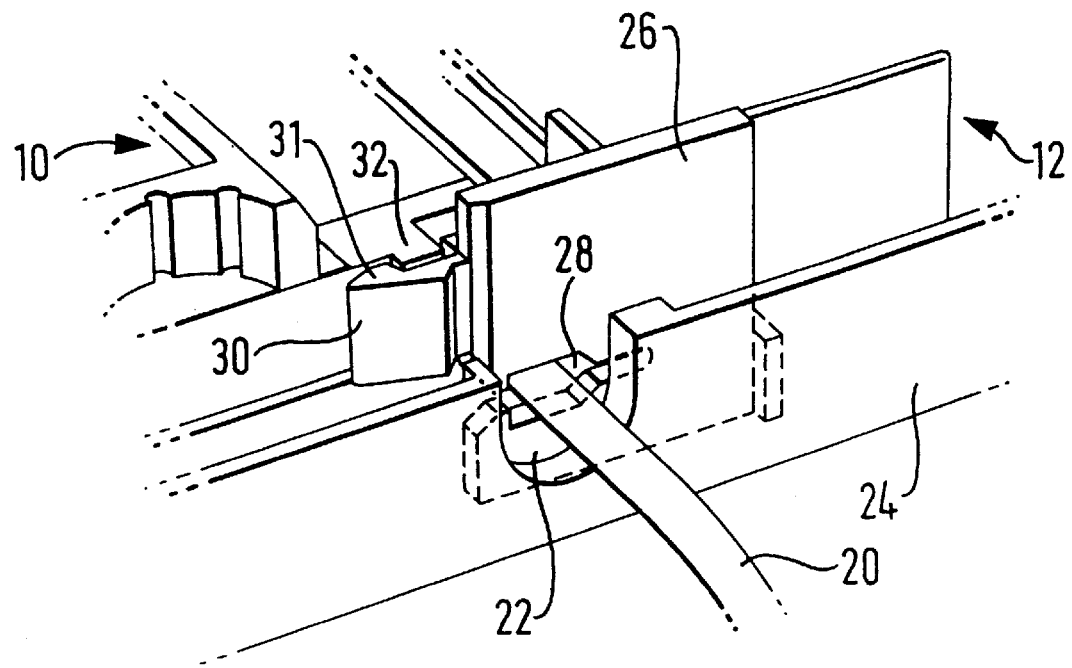
FIG. 2 shows the operating elements of the anti-freeflow device applied to the pump of FIG. 1.

Referring to FIG. 2, which shows a partial view of parts 10 and 12, on a larger scale than FIG. 1, to illustrate the operation of the anti-freeflow device in accordance with the invention, portion 20 of line 16 is shown passing through port 22 in wall 24 of part 12.

Sliding member 26 has a shaped aperture 28 of varying cross-sectional shape through which portion 20 of line 16 passes.

In the position shown in FIG. 2 the portion 20 of the infusion line 16 passes through a part of the aperture having a width substantially the same as the diameter of the portion 20 of the line 16 so that the line 16 is not constricted by the aperture 28 and is a loose fit within it.

A tongue 30 having a detent 31 is provided on sliding member 26 and is engaged by projection 32 formed in the body of part 10 when part 10 and part 12 are in full engagement. In this condition portion 18 of infusion line 16 is engaged between platen and pump fingers, and when the pump motor is not operating, portion 18 of line 16 is occluded by pressure applied to it by at least one of the pump fingers, preventing any inadvertent flow of infusate to the patient.

When part 10 is removed from part 12 however, portion 18 of infusion line 16 will be disengaged from the pump, and will no longer be occluded, and free flow of infusate to the patient might occur.

However this is prevented by the operation of the anti-freeflow device as follows.

As part 10 is withdrawn from part 12, projection 32 moves leftwardly as shown in FIG. 2 and draws the sliding member 26 leftwardly within its mounting slide in wall 24, by virtue of the engagement between the projection 32, and the tongue 30 and detent 31. This causes the narrower end of aperture 28 to engage with and constrict portion 20 of infusion line 16, prior to disengagement of portion 18 from the pump, thereby occluding portion 20 and preventing free flow of infusate to the patient from reservoir 14, which could otherwise occur once the part 10 had been fully withdrawn from part 12.

Tongue 30, molded in one piece with sliding member 26, is free to flex in a direction at right angles to the direction of travel of member 26, such that once member 26 has reached the limit of its leftward travel, (that limit being provided, for example, by a projection on the member 26 abutting a stop on the second part 12) tongue 30 flexes outwardly to permit release of the projection 32 by the detent 31 and continued leftward movement as part 10 is fully disengaged from part 12.

Figure 3:
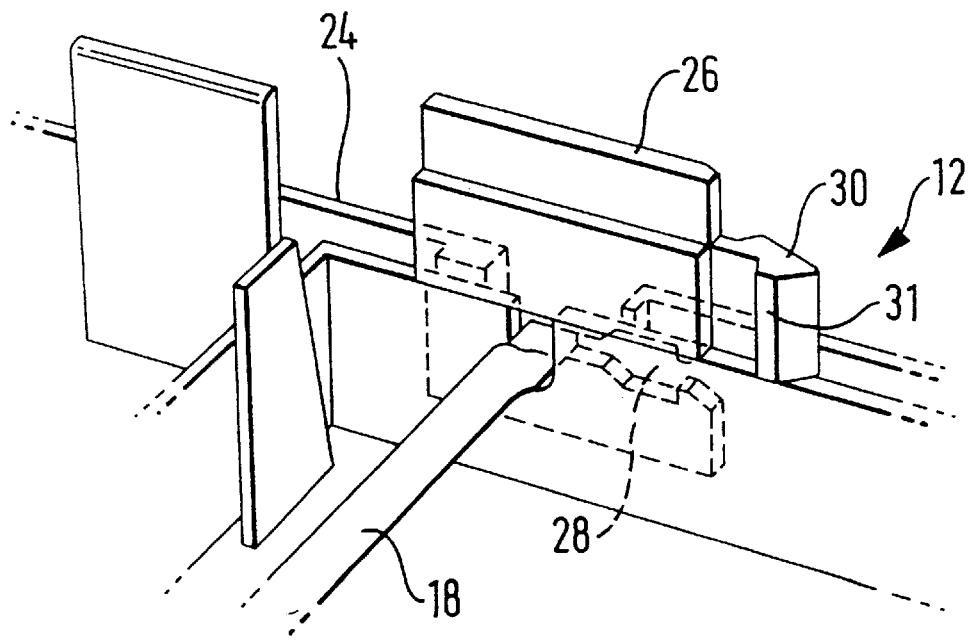
FIG. 3 shows a view of the device of FIG. 2 from the other direction.

FIG. 3 shows the view of the anti-freeflow device from the rear, with part 10 removed from part 12, and portion 20 of infusion line 16 fully occluded by the narrower part of aperture 28.

If parts 10 and 12 are subsequently re-attached, projection 32 engages tongue 30 and detent 31, causing sliding member 26 to move rightwardly in FIG. 2 (leftwardly in FIG. 3), so that portion 20 of infusion line 16 passes once again through the larger part of aperture 28, opening the line to flow of infusate to patient under control of the pump within part 10.

With part 12 removed from part 10, the sliding member 26 may be displaced manually by means of a tool which engages the recess in tongue 30 normally engaged by projection 32, if it is required either to remove or replace the infusate reservoir 14 and integral infusion line 16, or to recharge the reservoir with infusate through line 16.

Although sliding member 26 is shown with aperture 28 open at one end, in order to simplify the fitting and removal of the disposable infusate reservoir 14 and infusion line 16 in part 12, sliding member 28 may alternatively be provided with aperture 28 closed at both ends, completely encircling portion 20 of line 16, to ensure that portion 20 cannot become dislodged from aperture 28 in operation.

In the latter case sliding member 26 may also be a disposable element, provided upon the infusion line 16 of each replacement infusate reservoir 14 for fitment into the wall of part 12 when infusate reservoir 14 is changed.

It will be appreciated that use of an anti-freeflow device in accordance with the invention prevents inadvertent and possibly dangerous free flow of infusate from the infusate reservoir of a two-part infusion pump of the type described, when the two parts are separated.

As will be apparent various modifications may be made to the device described without exceeding the scope of the invention.

We claim:

1. An infusion set comprising a first part, a second part defining a cavity for housing a removable infusate reservoir and infusion line, the parts being releasably attachable together, and a closure member slidably mounted on the second part for closing the infusion line, the closure member defining an opening for passage of the infusion line therethrough, the closure member being operable, by detachment of the parts between a first, open infusion line position wherein the infusion line passes through a portion of the opening of dimension great enough to allow flow of infusate through the infusion line, and a second, closed infusion line position wherein the infusion line passes through a portion of the opening having a dimension sufficiently less than the diameter of the infusion line to occlude the infusion line.

2. An infusion set as claimed in claim 1 in which the opening is bounded by the closure member.

3. An infusion set as claimed in claim 1 in which the opening is unbounded at at least one end.

4. An infusion set as claimed in claim 1 in which the closure means has a tongue with a detent arranged to engage a projection on the first part to slide the closure means from the first to the second position as the parts are pulled apart and further arranged to release the closure means when the parts are fully detached.

5. An infusion set as claimed in claim 4 in which the tongue and detent are arranged to engage the projection on the first part to slide the closure means from the second position to the first position when the parts are re-attached.

6. An infusion set as claimed in claim 1 in which the closure means has a tongue with a detent arranged to engage a projection on the first part to slide the closure means from the first to the second position as the parts are pulled apart and further arranged to release the closure means when the parts are fully detached.

7. An infusion set as claimed in claim 6 in which the opening is bounded by the closure member.

8. An infusion set as claimed in claim 6 in which the opening is unbounded at at least one end.

9. An infusion set comprising:
   a first pump part including an infusion pump;
   a second reservoir part releasably attached to the first pump part including an infusate reservoir and at least a portion of an infusion line; and
   an infusion line closure member positionable between an open position permitting flow through the infusion line when the first pump part and the second reservoir part are attached and a second closed position restricting flow through the infusion line when the first pump part and the second reservoir part are detached.

10. An infusion set as claimed in claim 9 in which the infusion line closure member is slidably mounted to the second reservoir part.

11. An infusion set as claimed in claim 10 in which the closure member has an opening therethrough, and the infusion line passes through the opening, and further wherein the opening has a wide portion and a narrow portion such that the infusion line is engaged by the wide portion of the opening allowing infusate flow therethrough when the first pump part and the second reservoir part are attached one to the other and that the infusion line is engaged by the narrow portion of the opening restarting infusate flow therethrough when the first pump part and second reservoir part are detached one from the other.

12. An infusion set as claimed in claim 11 in which the closure member includes a resilient tongue with a detent and the pump part includes a projection adapted to engage the closure member tongue detent such that the closure member translates from an infusate line flowing position to an infusate line restricted position when the first pump part and the second reservoir part are separated.

13. An infusion set as claimed in claim 12 in which the projection of the first pump part is further adapted to the tongue and detent of the closure member to translate the closure member from the infusate restricted position to the infusate flowing position when the first pump part and second reservoir part are attached one to the other.

14. An infusion set as claimed in claim 13 further including a manual tool adapted to manually translate the closure member.

15. An infusion set comprising a first part, a second part for containing an infusate reservoir and infusion line, the parts being releasably attachable together, and means for closing the infusion line, the closure means being slidably mounted on the second part between a first, open infusion line position and a second, closed infusion line position operable by detachment of the parts to close the infusion line, wherein the closure means has a tongue with a detent arranged to engage a projection on the first part to slide the closure means from the first to the second position as the parts are pulled apart and further arranged to release the closure means when the parts are fully detached, and further wherein the infusion line passes through an opening in the closure means and the closure means is further mounted such that in the first position the infusion line passes through a portion of the opening of dimension great enough to allow flow of infusate through the infusion line and in the second position the infusion line passes through a portion of the opening having a dimension sufficiently less than the diameter of the infusion line to occlude the infusion line.

16. An infusion set comprising:
  a first pump part including an infusion pump;
  a second reservoir part releasably attached to the first pump part, the second reservoir part defining a cavity to house a removable infusate reservoir and at least a portion of an infusion line; and
  an infusion line closure member positionable between an open position permitting flow through the infusion line when the first pump part and the second reservoir part are attached and a second closed position restricting flow through the infusion line when the first pump part and the second reservoir part are detached.

17. An infusion set as claimed in claim 16 in which the infusion line closure member is slidably mounted to the second reservoir part.

18. An infusion set as claimed in claim 17 in which the closure member has an opening for passage therethrough of an infusion line, and further wherein the opening has a wide portion and a narrow portion such that the infusion line is engaged by the wide portion of the opening allowing infusate flow therethrough when the first pump part and the second reservoir part are attached one to the other and that the infusion line is engaged by the narrow portion of the opening restarting infusate flow therethrough when the first pump part and second reservoir part are detached one from the other.

19. An infusion set as claimed in claim 18 in which the closure member includes a resilient tongue with a detent and the pump part includes a projection adapted to engage the closure member tongue detent such that the closure member translates from an infusate line flowing position to an infusate line restricted position when the first pump part and the second reservoir part are separated.

20. An infusion set as claimed in claim 19 in which the projection of the first pump part is further adapted to the tongue and detent of the closure member to translate the closure member from the infusate restricted position to the infusate flowing position when the first pump part and second reservoir part are attached one to the other.

21. An infusion set as claimed in claim 20 further including a manual tool adapted to manually translate the closure member.

* * * * *